United States Patent [19]

Gruenberg

[11] Patent Number: 4,629,686
[45] Date of Patent: * Dec. 16, 1986

[54] APPARATUS FOR DELIVERING A CONTROLLED DOSAGE OF A CHEMICAL SUBSTANCE

[75] Inventor: Micheal L. Gruenberg, Chicago, Ill.

[73] Assignee: Endotronics, Inc., Minneapolis, Minn.

[*] Notice: The portion of the term of this patent subsequent to Oct. 21, 2003 has been disclaimed.

[21] Appl. No.: 388,136

[22] Filed: Jun. 14, 1982

Related U.S. Application Data

[63] Continuation-in-part of Ser. No. 350,135, Feb. 19, 1982, abandoned.

[51] Int. Cl.[4] .......................... A01N 1/02; C12M 1/36; C12M 3/00
[52] U.S. Cl. .................................... 435/1; 435/289; 435/283; 435/284
[58] Field of Search ................. 222/52, 56; 364/413, 364/414, 415, 416; 435/1, 289, 291, 813, 283, 284, 287; 604/50, 66

[56] References Cited

U.S. PATENT DOCUMENTS

| | | | |
|---|---|---|---|
| 2,690,178 | 9/1954 | Bickford | 604/66 |
| 3,531,258 | 9/1970 | Merrifield et al. | 422/116 |
| 3,545,221 | 12/1970 | Swenson et al. | 435/1 X |
| 3,557,077 | 1/1971 | Brunfeldt et al. | 422/108 |
| 3,607,646 | 9/1971 | de Roissart | 435/1 |
| 3,632,473 | 1/1972 | Belzer | 435/1 |
| 3,647,390 | 3/1972 | Kubodera et al. | 422/116 X |
| 3,871,361 | 3/1975 | Kamen | 604/66 X |
| 3,926,737 | 12/1975 | Wilson et al. | 435/289 X |
| 4,064,015 | 12/1977 | Nyiri et al. | 435/3 |
| 4,167,450 | 9/1979 | Chesbro et al. | 435/3 |
| 4,231,354 | 11/1980 | Kurtz et al. | 604/66 X |
| 4,280,494 | 7/1981 | Cosgrove, Jr. et al. | 604/66 X |
| 4,299,919 | 11/1981 | Jellinek | 435/289 X |
| 4,308,866 | 1/1982 | Jelliffe et al. | 364/413 X |
| 4,392,849 | 7/1983 | Petre et al. | 604/66 |

Primary Examiner—David M. Naff
Assistant Examiner—Randall E. Deck
Attorney, Agent, or Firm—Kinney & Lange

[57] ABSTRACT

An apparatus is disclosed which delivers a dosage of a chemical substance preferably to a biological tissue in such a controlled manner that the concentration affecting the biological tissue is known at each and every point in time. The apparatus includes a plurality of vessels with each vessel containing a different concentration of the chemical substance. A valve has a plurality of inlets and a single outlet wherein each inlet is connected to a corresponding vessel. The biological tissue is preferably held within a chamber for treatment with the chemical substance. A pump positioned preferably between the valve and the biological tissue provides a transport force for delivering the chemical substance to the tissue. The valve and the pump are controlled by a computer control system which determines which inlet of the valve is fluidly connected to the outlet for providing a preselected concentration of the chemical substance to the tissue such that the concentration of the chemical substance affecting the tissue is controlled at each and every point in time.

20 Claims, 8 Drawing Figures

APPARATUS FOR DELIVERING A CONTROLLED DOSAGE OF A CHEMICAL SUBSTANCE

CROSS REFERENCE TO RELATED APPLICATION

The present application is a continuation-in-part of pending application Ser. No. 350,135, filed Feb. 19, 1982 entitled "Process for Controlling Patterns of Chemical Stimuli Administration to Biological Tissue," now abandoned.

BACKGROUND OF THE INVENTION

1. Field of the Invention

The present invention relates to apparatus which controls processes that supply a chemical substance to a particular location. In particular, it relates to a process that supplies a chemical substance such that the concentration of the chemical substance affecting the location is controlled at each and every point in time and is known at each and every point in time and where the parameters of various amplitudes, durations, rate dynamics, periodicities, frequency of oscillations, notch, plateau, bimodal, and phase relationships of the chemical substance can be controlled and manipulated with respect to time.

2. Description of the Prior Art

The maintenance of biological tissue, such as organs, isolated from their natural nutrient supply is of great importance. A significant amount of research has been done with regard to organs that have been removed from a body. The research is quite varied and ranges from simply trying to keep the particular organ alive outside of the body to studying the complex responses of the isolated organ to various chemical stimuli.

Typically, the organ is placed in a chamber and its biological function supported by some type of culture medium. Initially, the system used to keep an organ alive was a static one wherein the nutrients were initially mixed in the culture medium and were never replenished. This type of system was limited in its ability to sustain an organ in a biologically alive state since the culture medium very quickly became contaminated from the organ's waste products and natural secretions.

Deficiencies of the static system led to the development of a dynamic system wherein the culture medium and the chamber holding the organ was replenished and was capable of sustaining biological life for a significantly extended period of time. These systems are commonly referred to as perfusion, perifusion or superfusion systems and have significantly increased the time available for studying organs and other tissue outside of the body.

The perifusion system is a system wherein the organ is surrounded by a culture medium containing nutrients that are absorbed by the organ. The perfusion system supplies nutrients to the organ through the organ's cardiovascular system. The superfusion system includes a system that both perfuses and perifuses nutrients to the organ.

Typically, the dynamic systems include a chamber in which the organ or other tissue is placed. The chamber has an inlet for providing nutrient-containing culture medium and an outlet for removing culture medium at a rate which preferably keeps the volume of the culture medium constant within the chamber. The dynamic systems have several advantages. First, conditions in the dynamic systems more closely resemble conditions within the body than the conditions in a static system through the continuous turnover of the medium thereby minimizing the effect of secretion and waste product accumulation. Second, the organ can be presented to different reagents without removal of the organ from the chamber. Third, the effects of nutrients and other chemical stimuli may be studied by collecting samples from the outlet of the chamber and analyzing such samples.

However, the perfusion, perifusion and superfusion systems of the prior art have several limitations. First, only a static concentration of a chemical stimuli can be supplied to the organ such that the concentration is known at every point in time. Varying the concentration dynamically by providing "pulses" of chemical stimuli results in unknown concentrations with respect to time of the chemical stimuli affecting the organ in the culture chamber. Consequently, research to determine the response of an organ to various concentrations of chemical stimuli using a dynamic system has been often times ineffective.

Second, since only a static or pulsed concentration of a nutrient or other chemical stimuli can be presented to the organ, overdose or underdose has been a frequent result. In trying to sustain organs in a biologically alive state, the supply of the proper concentration of nutrients to the organ as the organ's need for nutrients changes with respect to time is extremely important in extending the biological life of the organ or in attempting to analyze the response of an organ to a chemical stimuli in a dynamic situation.

Some prior art processes which increase the concentration of a drug or stimuli being presented to a biological tissue increase the concentration in a pulse-type manner. The pulse-type process is a flow through system where a constant concentration "x" of the drug or stimuli is continually delivered to the tissue in a supportive media. To increase the concentration affecting the tissue, a specific volume of a concentration "y" of the drug or stimuli greater than concentration "x" is injected into a holding chamber which houses the tissue. At the time of injection, if the volume in the holding chamber is known and the volume of supportive medium containing concentration "y" injected is known, then the initial concentration at the time of injection will also be known. However at any time after injection, the concentration will decrease as the supportive media containing concentration "x" continues to flow through. Thus, the concentration affecting the tissue is unknown after the time of injection. Therefore, the effect that the drug or stimuli is having on the tissue during the change is not known since any assay of the response emitted by the tissue during this time cannot be correlated to any definite concentration of the drug or stimuli. The problem of not being able to determine the concentration after injection is further amplified when an injection is made before the concentration in the holding chamber returns back to concentration "x". In this situation, the concentration affecting the tissue at the point in time of the second injection is not known.

In other prior art processes, the concentration affecting the tissue is increased or decreased in a flow through system in a step-like manner. To accomplish a step-like increase or decrease in concentration, the flow of the concentration affecting the tissue is stopped and a second different concentration is introduced into the holding chamber and the concentration in the holding chamber is allowed to equilibrate to the second concentration. The time required to reach equilibrium and the concentration affecting the tissue during this time is not known.

Drugs and stimuli fluctuate in various manners in an intact organism. These prior art processes are not able to emulate these fluctuations and thus cannot provide a physiological environment for the isolated tissue. In addition, it is desirous to selectively manipulate these fluctuations to study the effects of different amplitudes, durations and frequencies of drugs and stimuli.

SUMMARY OF THE INVENTION

The present invention is an apparatus that delivers a chemical substance in a controlled manner to a location such that the concentration of the chemical substance affecting the location is controllable at each and every point in time. The apparatus includes a plurality of vessels, each vessel containing a different known concentration of the chemical substance. A valve having a plurality of inlets and a single outlet and each inlet is fluidly connected to a particular vessel of a different known concentration. Preferably, the location includes a culture chamber holding a biological tissue in a culture medium for presentation to the chemical substance. The culture chamber is fluidly connected to the outlet of the valve and preferably a pump provides a transport force to the chemical substance. The valve and the pump are preferably controlled by a computer control system which selects a predetermined inlet for fluid concentration with the outlet of the valve. The computer control system also selects a flow rate and operates the pump such that the flow rate is achieved. Further, the computer control system determines the concentration affecting the tissue being delivered to the location.

DETAILED DESCRIPTION OF THE PREFERRED EMBODIMENT

Figure 1:
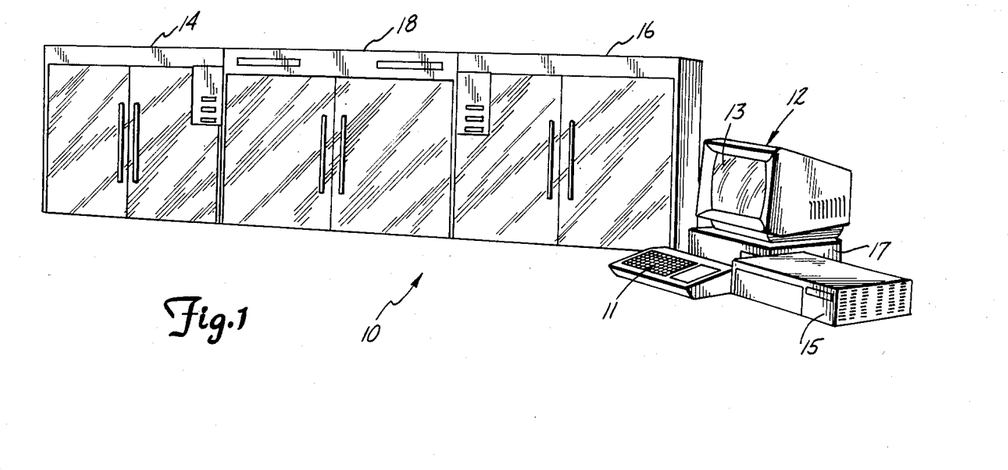
FIG. 1 is a perspective view of the apparatus of the present invention.

The apparatus of the present invention is generally indicated at 10 in FIG. 1. Throughout the figures, like reference characters are used to indicate like elements. The specification and figures of pending application Ser. No. 350,135, filed Feb. 19, 1982 entitled "Process for Controlling Patterns of Chemical Stimuli Administration to Biological Tissue", abandoned, is hereby incorporated by reference. The apparatus 10 includes a programmed digital computer control system 12 and the physical plant for treating a biological tissue preferably housed in a plurality of cabinets. The computer control system 12 includes a keyboard and microcomputer unit 11, a CRT display 13, a minidisk unit 15 and an I.O. unit 17. The physical plant preferably contains a left cabinet 14 and a right cabinet 16, the contents of the right cabinet being more fully illustrated in FIG. 2. The left cabinet is the mirror image of the right cabinet and contains the same contents. A center cabinet 18 is positioned between the left and right cabinets 14 and 16 as illustrated in FIG. 1 with the contents of the center cabinet 18 being more fully illustrated in FIG. 3.

In one successful embodiment, the keyboard and microprocessor unit 11 is a N.E.C. PC8001A, the CRT display 13 is a Model VC1202-DH(A) by N.E.C., the minidisk unit 15 is a N.E.C. PC8031A, and the I.O. unit 17 is a N.E.C. PC8012A, all by Nippon Electric Co.

The apparatus of the present invention is preferably used to deliver a preselected concentration of a chemical stimuli or drug, such as a nutrient or a hormone, to a biological tissue in a predetermined controlled manner such that the concentration of the chemical stimuli or drug affecting the tissue is controlled and known at each and every point in time.

Figure 2:
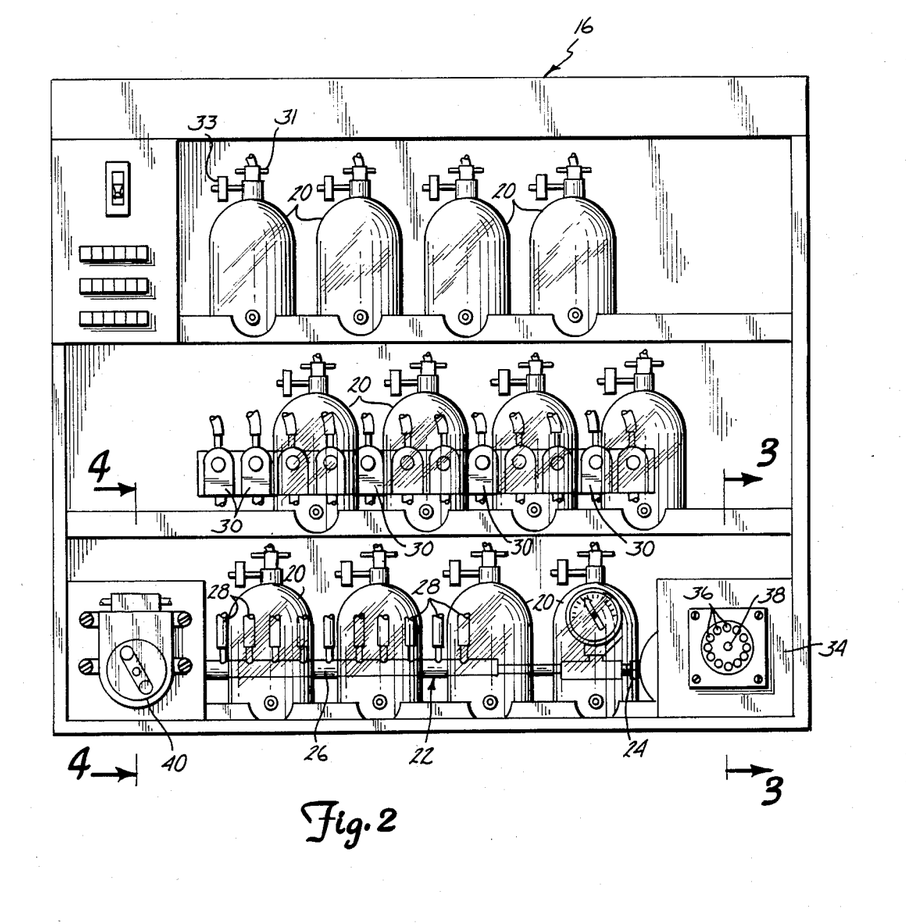
FIG. 2 is a front view of the right cabinet containing vessels, pump and valve.

In FIG. 2, wherein the right cabinet 16 is more fully illustrated, a plurality of flasks 20 hold different concentrations of the particular drug or stimuli in a supportive medium. The particular concentration in each flask 20 is determined prior to any experiment through the computer control system 12.

Figure 4:
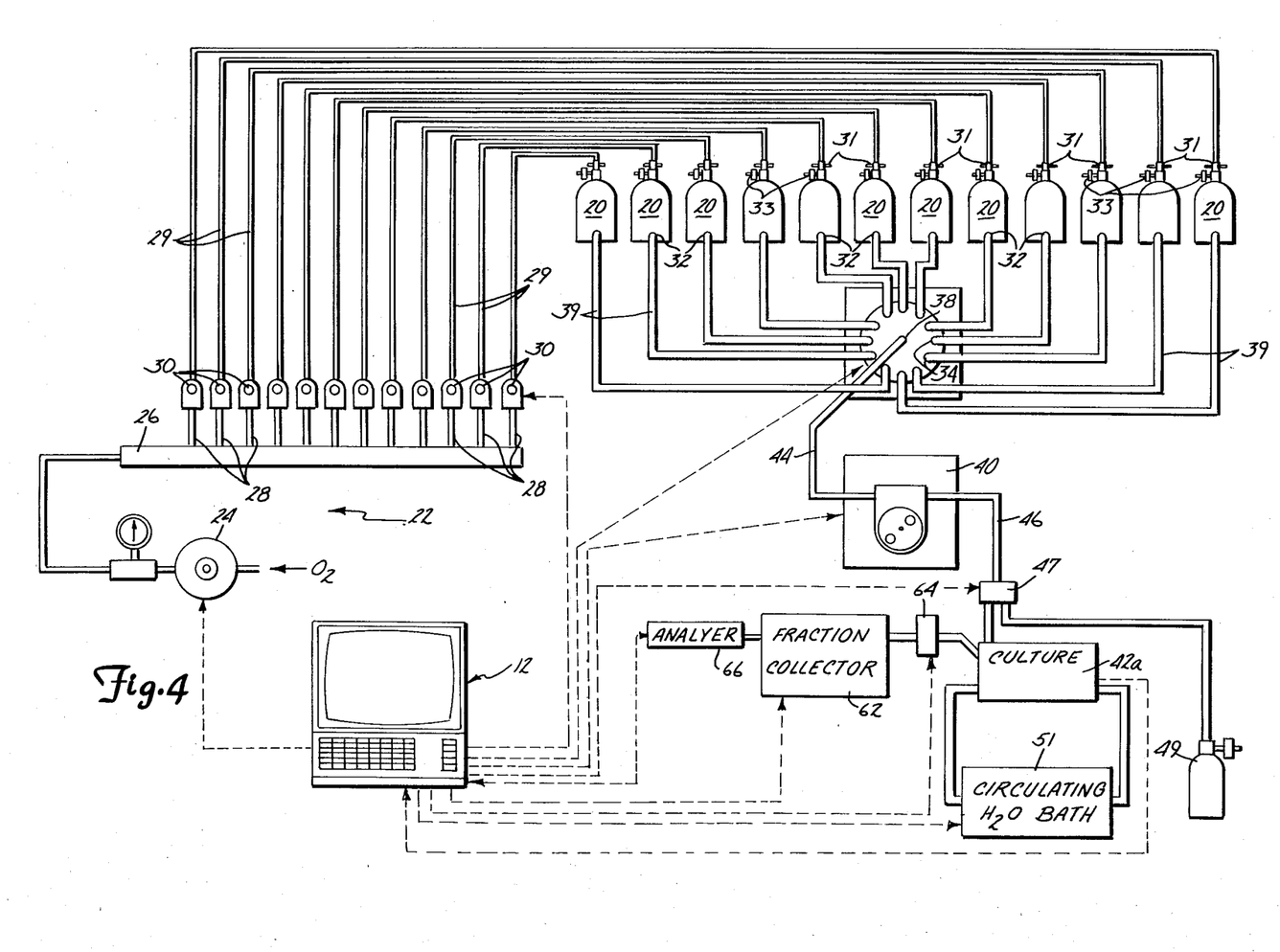
FIG. 4 is a diagrammatical view of the apparatus of the present invention.

The drug or stimuli is typically mixed with a supportive medium. The concentration of drug or stimuli required in each flask is achieved by mixing the drug or stimuli with the supportive medium. The culture medium with the drug or stimuli is also equilibrated with $CO_2$ in oxygen. The $CO_2$ in oxygen is delivered to each flask through a gas delivery system generally indicated at 22, as best illustrated in FIG. 4. The gas is metered into the gas delivery system by a pressure regulator mechanism 24. The pressure regulator mechanism maintains a constant predetermined delivery pressure. A manifold 26 distributes the gas into individual gas lines 28 made of suitable conduit. Each line 28 is connected to a corresponding solenoid valve 30. The solenoid valve 30 is connected to the top of each flask 20 by a gas line 29 with a suitable connector. Prior to the connection of the gas line 29 to the flask 20, a sterilizing filter 31 is positioned inline. The gas as introduced into the flask 20 through a gas diffuser such as a fritted glass tube (not shown) that extends into the culture medium within the flask 20. Each flask 20 has a pressure relief valve with a sterile filter 33.

It is desirous to diffuse gas into one or more predetermined flasks 20 at any one time. Diffusion of the gas in one or more flasks 20 is accomplished by opening or closing corresponding solenoid valves 30 under computer control. The regulator 24 maintains the predetermined gas pressure in any line 29 regardless of how many solenoid valves are opened or closed.

Each flask 20 preferably has a lower outlet 32 which is fluidly connected to a corresponding inlet in a valving mechanism 34 by suitable tubing 39. The valving mechanism 34 has a plurality of inlets 36 and a single outlet 38. In one successful embodiment of the present invention, the valve has twelve inlets. The valving mechanism fluidly connects any inlet 36 to the single outlet 38 under the control of computer control system 12. The valve 34 maintains a sterile seal to all lines not connected to outlet 38. All material used for surfaces in contact with the chemical stimuli is chemically inert.

Further, the chemical stimuli with supportive medium is maintained within the apparatus in a closed sterile environment.

The outlet 38 of the valving mechanism 34 is connected with tubing 44 to a pumping mechanism 40, preferably a peristaltic pump having a variable flow rate delivery under the control of the computer control system 12. The peristaltic pump 40 provides a transport force for delivering the supportive medium with the chemical stimuli to the tissue. In one successful embodiment, the peristaltic pump has a capability of delivering accurately to within ±0.01 milliliters in any time interval.

The peristaltic pump 40 delivers the drug or chemical stimuli in the supportive medium to an inner chamber of a culture chamber 42a and is fluidly connected to the inner chamber with tubing 46. The medium is delivered to the inner chamber through a dropping tube 41 and exits through opening 43.

Figure 5:
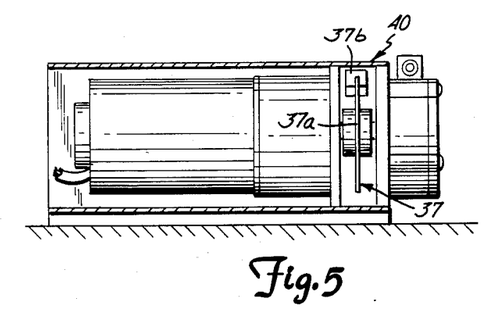
FIG. 5 is a side cross sectional view of the pump with portions shown whole for clarity.
Figure 6:
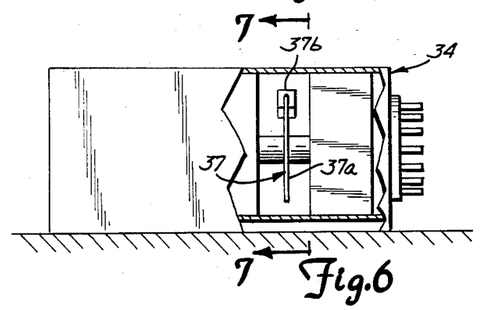
FIG. 6 is a side view of the valve with portions broken away to show an inlet location mechanism.
Figure 7:
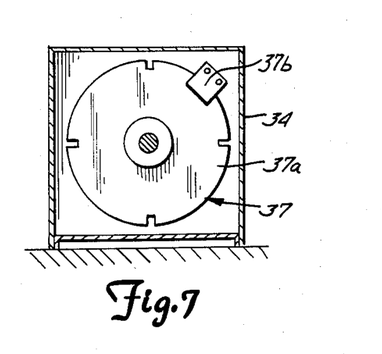
FIG. 7 is a front view of the location mechanism taken along the line 6—6 in FIG. 6.

Both the peristaltic pump 40 and the valving mechanism 34 have a location indication mechanism 37, as illustrated in FIGS. 5 and 6, respectively. A flat disc 37a is fixedly attached to a rotating portion of the pump and the valve and rotates therewith. The flat disc 37a has a position indicator 37b which interrupts a stationary photocell (not shown). In the case of the pump 40, the position indicator 37b indicates to the computer control system 12 the number of revolutions of the pump 40 and therefore the flow rate. In the case of the valve 34, the position indicator provides a reference point that indicates the relative position of all of the inlets to the computer control system 12.

A purge valve 47, illustrated in FIG. 4, is positioned prior to the culture chamber. The purge valve 47 permits purging of the lines 44 and 46 when changing from one concentration of the chemical stimuli to another concentration. Preferably, the chemical stimuli is purged into a waste bottle 49 with a pressure relief valve having a sterile filter. The pump 40 has sufficient capacity to purge tubing 44 and 46 quickly and still deliver the stimuli at slower delivery rates within ±0.01 milliliters.

The tubing 39, 44 and 46 is of a small diameter with precise tolerances. A small diameter is needed so that a minimum amount of volume of supportive medium and chemical stimuli is contained within the tubing. In one working embodiment, the tubing is a silicone tubing having an inner diameter of 1/32 of an inch. A minimum diameter is desirous in tubing 39 since only the volume of supportive medium within the flask 20 is being diffused with oxygen and the small diameter minimizes any ungassed supportive medium. Precise tolerances of the tubing 44 and 46 are desirous to calculate the volume being delivered by pump 40 and to minimize the amount that is purged during a flask 20 changeover.

The culture chamber 42a is an airtight double walled flask having an inner chamber 48 for holding a biological tissue. The temperature at which the inner chamber 48 is held is controlled by circulating a fluid, such as water or oil, in a jacket 50 between the inner wall of the inner chamber 48 and the outer wall of the flask. The water or oil is circulated from a reservoir bath 51 wherein the temperature of the water or oil is controlled preferably within ±0.3° F.

Figure 3:
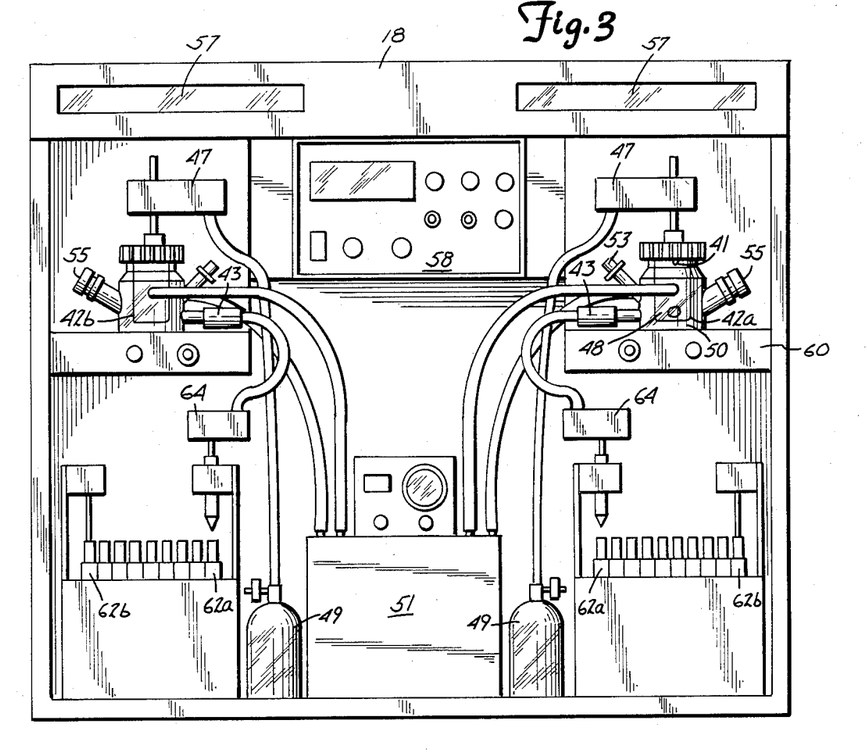
FIG. 3 is a front view of the center cabinet containing the culture chamber.

The culture chamber 42a, as illustrated in FIG. 3, includes side arms 53, 55 for probes to sense temperature and pH with a microprocessor controlled device 57, and analyze for oxygen content in the supportive medium through an oxygen meter 58.

With the culture chamber 42a being airtight, any amount of supportive medium pumped into the culture chamber will force the same amount out of the culture chamber.

The culture chamber is positioned on a magnetic stirrer 60 which is important for proper diffusion of the incoming concentration of chemical stimuli in supportive medium within the culture chamber. Preferably, the stirrer is operable at slow speeds and is capable of long duty cycles. In addition, the stirrer is of a type that minimizes heat transfer to the culture chamber.

From the culture chamber, the supportive medium is transported to a first fraction collector 62a. The fraction collector 62a includes a plurality of test tubes wherein the supportive medium is dropped into a predetermined test tube. The supportive medium is exposed to the atmosphere as it is placed in predetermined test tubes. To ensure sterility, the supportive medium is protected by a sterile dispenser 64. The sterile dispenser maintains the air in a sterile state through which the supportive medium is conveyed using ultra-violet light.

The supportive medium is removed from the test tube automatically or manually to an analyzer 66. The results provided by the analyzer 66 are recorded by the computer control system 12.

As will be noted from FIG. 3, the central cabinet 18 has a second culture chamber 42b and a second fraction collector 62b. The central cabinet 18 is divided substantially into two halves with one being the mirror image of another each half sharing the same reservoir bath 51. Concentrations of the drug or stimuli are delivered from left cabinet 14 to the culture chamber 42b. Thus, the apparatus of the present invention allows the user to simultaneously run two experiments, preferably with one being a control. This allows data to be gathered simultaneously to the benefit of the experimenter in obtaining more precise results and analysis of how a particular tissue reacts to a certain concentration of a drug or chemical stimuli.

The computer control system 12 shown in FIG. 1 and diagrammatically illustrated in FIG. 4, controls the various process steps of the apparatus of the present invention as indicated by various broken lines. The computer control system 12 controls the operation of the solenoid valves 30, the valving mechanism 34, the pump 40, the fraction collectors 62a and 62b, along with recording and monitoring other data from probes within the culture chamber, such as temperature, pH, and oxygen level. In a simple experiment, the operator uses keyboard 11 to enter into the computer control system 12 the starting concentration in which the tissue is initially immersed in the culture chamber, and the various concentrations which he would like to deliver to the tissue in the culture chamber in a specified time interval. Based upon a stored program in computer memory, the computer control system 12 informs the operator what concentrations the operator should mix in the flasks 20 by displaying messages on CRT display 13. Based upon input signals from keyboard 11 and the stored program (and in some cases on feedback signals from sensors), the computer control system 12 automatically delivers the predetermined concentrations to the culture chamber by controlling the operation of the valve 34 and the pump 40. The computer control system 12 will also record data from the sensors within the culture chambers and correlate the data to particular time periods, therefore, particular concentrations of the drug, and analyze the fractions collected by the fraction collector, allowing the experimenter to see almost immediately (on CRT display 13) the results and effects of a change in concentration and how it relates to the simultaneously run control experiment.

Through the stored program in the computer control system 12, the operator can input into the computer control system 12 through the keyboard 11 several experiments. During the course of the experiments, the operator, by selecting function keys on the keyboard, displays various indicia indicating the progress of the experiment and the data recorded.

In a more complicated experiment, the apparatus of the present invention can be used as a closed loop control for preservation of organ transplants. Typically, such organs using prior art processes for preservation can survive for very limited periods of time once they have been removed from the donors using apparatus existing prior to the present invention. These prior art apparatus use a static drug dose system and cannot fluctuate the delivery of nutrients according to the needs of the organ. The needs of the organ vary with respect to time as has been documented. Therefore, an underdose or an overdose of these nutrients will occur at any point in time. Using the apparatus of the present invention, the optimal nutrient needs or dosages are determined through procedures previously discussed. Then the computer control system 12 is programmed to provide the organ with appropriate dosages of the nutrient depending on the data being emitted by the organ and being monitored by the computer control system. It has been demonstrated using the apparatus of the present invention that rat ovaries can be maintained and remain physiologically viable during a simulated four-day cycle in-vitro. They responded to a series of chemical stimuli which mimic the in-vivo condition of the rat by ovulating at the end of the four-day cycle. In addition, the ovaries grew and secreted substances very similar to ovaries remaining in-vivo. Persons skilled in the art will recognize that this is a remarkable accomplishment over prior art apparatus. Furthermore, there was no indication at the end of the experiment that the ovaries would not continue to respond in this manner for a further extended period of time.

Another application of the apparatus of the present invention includes intravenous administration of drugs or the like. Again, the intravenous administration of a drug to a patient is typically a constant dosage administration. Consequently, once a predetermined administration of the drug has been determined, the apparatus of the present invention can be used to deliver a desired drug dosage in response to the needs of the patient which the computer control system 12 may monitor physiologically or otherwise.

Since it is known that all biological phenomena are physiochemical, there will always be an appropriate dynamic description. Utilizing the apparatus of the present invention, it is now possible to study the effects of these dynamics and to discover how they control cellular activities. The apparatus is then ultimately used to control the response of cells for therapeutic purposes or to achieve optimally desired responses.

A further application of the present invention is within the field of controlled crystal growth. Semiconductors, certain silicone and vinyl polymers and specialty paints for military use are produced using prior art processes and apparatus which attempt to grow organic and inorganic crystals in a controlled manner. Using the apparatus of the present invention, administration of the substance forming the crystal is performed in a controlled manner with the crystal being grown within a chamber. The optimum temperature for the particular crystal growth desired is easily controlled while amounts of the substance forming the crystal is delivered in a predetermined manner to control the proper growth of the crystal. In addition, impurities which impart desirable characteristics to the crystal are also added in a controlled manner using the present invention.

The change in concentration of the substance within the culture chamber in response to a known supply substance concentration being delivered to the culture chamber with a known volume at a known rate can be readily determined by use of the system in conjunction with a digital computer.

In the present process a certain rate dependent volume was removed from the culture chamber during a known time interval. Simultaneously, a drop of another rate dependent volume is being formed at the top of the culture chamber. Eventually, this drop enters the culture chamber and equilibrates with the substance in the culture chamber.

To initiate the simulation sequence, the following parameters were defined:
Culture Chamber Volume (V)—ml
Culture Chamber Starting Concentration ($C_i$)—units/ml
Supply Drug Starting Concentration in Holding Flasks ($C_s$)—units/ml
Rate of Fluid Delivery (R)—ml/hr
Integration Interval (t)—seconds With these parameters defined, the following loops were programmed in the digital computer to simulate the process. The following jobs were performed during each loop for each chemical stimuli:

1. The total number of units ($U_t$) in the culture chamber was determined ($U_t = C_i$ units/ml $\times V$ ml).
2. A volume ($V_R$) was removed from the culture chamber. $V_R$ is a function of R and t $$\left( V_R = \frac{R \text{ml/hr} \times t \text{ sec}}{3600 \text{ hr/sec}} \right).$$

3. The new volume of the culture chamber was determined ($V = V - V_R$).
4. The amount of units removed ($U_R$) from the culture chamber with $V_R$ was determined. $U_R$ is a function of $C_i$ and $V_R$ ($U_R = (C_i$ units/ml$)(V_R$ ml$)$).

5. The new $U_t$ in the culture chamber was determined ($U_t = U_t - U_R$).
6. A volume was added to the culture chamber ($V_A$) from the holding flask. If the culture chamber was airtight, $V_A$ would be equivalent to $V_R(V_A = V_R)$.

7. The new volume of the culture chamber was determined ($V = V + V_A$).
8. The amount of units added to the culture chamber ($U_A$) with $V_A$ was determined $(U_A=(C_s \text{ units/ml})(V_A \text{ ml}))$ 9. The new $U_t$ in the culture chamber was determined $(U_t=U_t+U_A)$.

10. The new $C_i$ was determined $$\left( C_i = \frac{U \text{ units}}{V \text{ ml}} \right)$$

When the culture chamber volume is kept constant, the concentration of any diffusable substance can be determined mathematically (equation (1)). This equation is derived from the computer-aided analysis of the process.

$$\left( C_{(t)} = C_s + (C_i - C_s)e^{-\frac{Rt}{V}} \right) . \quad (1)$$

$C_{(t)}$=concentration in culture chamber at time t
$C_s$=concentration of chemical stimulus in holding flask (final culture chamber concentration at $t = \infty$)
$C_i$=initial culture chamber concentration (t=0)
R=rate of supply substance delivery from holding flask to culture chamber (ml/hr)
V=volume of media in culture chamber (ml)
t=time (hrs)

To test the ability of equation (1) to accurately predict the concentration of the substance in the culture chamber when either a higher or lower concentration of the same drug was being delivered to the culture chamber at a constant rate, the following experiments were conducted. A dye, methyl orange (MO), was selected as the supply substance in these experiments because: (1) the concentration of the dye in the culture chamber could be easily assayed by measuring percent transmission at a maximum absorbance of 460 nanometers utilizing a spectrophotometer, and (2) at the completion of the assay, the sample of culture chamber fluid could be placed back into the culture chamber. This is important because it allowed continuous sampling over time without altering any of the parameters in equation (1) (i.e., culture chamber volume and $C_i$).

To test the ability of equation (1) to predict changes in culture chamber concentration when a higher concentration of the same drug was delivered at a constant rate from the holding flask, 100 ml of a standardized solution was placed in the holding flask. This solution of MO was adjusted so that it produced a reading of 10% transmission and was considered to be a 100% concentrated solution. 20 ml of distilled water (100% transmission) was placed in the culture chamber and was considered a 0% concentrated solution. The values between 10 and 100 percent transmission lie on the linear portion of a standard curve with a correlation coefficient of 0.99995 comparing known concentrations of MO and percent transmission. The 100% solution was pumped into the culture chamber at a rate of 18.5 ml/hr. At 15 minute intervals over a period of two hours, the pump was turned off and a 2 ml sample from the culture chamber was removed and assayed with a photospectrometer. The percent transmission was converted to optical density and the concentration recorded from the standard curve. The sample was then replaced in the culture chamber and the pump restarted.

To test the ability of equation (1) to predict changes in culture chamber concentration when a lower concentration of the supply drug was delivered from the holding flask, 100 ml of distilled water (0% concentration) was placed in the holding flask. 20 ml of a 100% concentrated solution of MO was placed in the culture chamber. The 0% concentrated solution was then pumped into the culture chamber and the methyl orange concentration determined as described above. The results indicated that equation (1) can be used as an expression to describe the present process.

With the capability of being able to accurately predict concentration changes in the culture chamber, it is now possible to emulate any data where a diffusable substance concentration is plotted as a function of time, in the culture chamber. With the initial concentration of the substance in the culture chamber known and the value of the desired final concentration in the culture chamber over a known time interval also known ($C_{s \cdot t}$). The concentration of the substance to be placed in the holding flask can be determined by a manipulation of equation (1) to derive equation (6).

$$c_{(t)} = C_s + (C_i - C_s)e^{-\frac{Rt}{V}} \quad (1)$$

since $C_{s \cdot t} = C_{(t)}$, substituting $$C_{s \cdot t} = C_s + (C_i - C_s)e^{-\frac{Rt}{V}} \quad (2)$$

factoring:

$$C_{s \cdot t} = C_s + C_i e^{-\frac{Rt}{V}} - C_s e^{-\frac{Rt}{V}} \quad (3)$$

subtracting $C_i e^{Rt-/V}$ from each side:

$$C_{s \cdot t} - C_i e^{-\frac{Rt}{V}} = C_s - C_s e^{-\frac{Rt}{V}} \quad (4)$$

factoring:

$$C_{s \cdot t} - C_i e^{-\frac{Rt}{V}} = C_s(1 - e)^{-\frac{Rt}{V}} \quad (5)$$

solving for $C_s$:

$$C_s = \frac{C_{s \cdot t} - C_i e^{-\frac{Rt}{V}}}{1 - e^{-\frac{Rt}{V}}} \quad (6)$$

Figure 8:
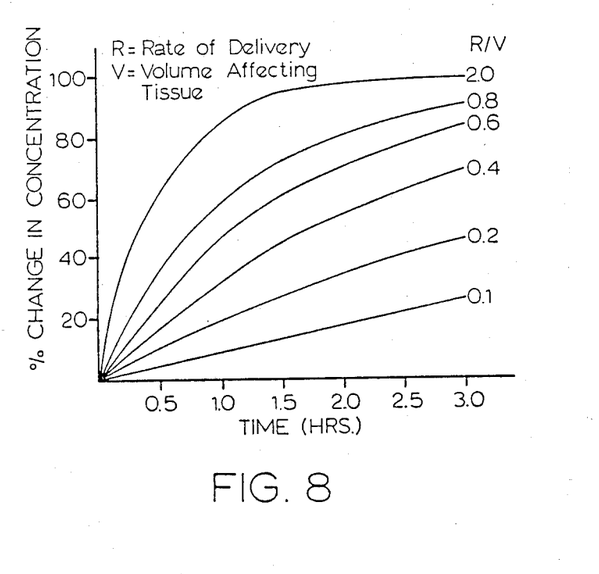
FIG. 8 is a graph illustrating a plurality of possible R/V ratios.

To more precisely emulate in-vivo conditions, a desired rate of delivery (R) and a desired volume (V) affecting the tissue in the culture chamber must be determined. In other words, if it is desirous to change the concentration of the substance within the culture chamber from the initial concentration ($C_i$) to a different concentration ($C_{(t)}$) linearly with respect to time, the change from $C_i$ to $C_{(t)}$ is a function of R and V. As shown graphically in FIG. 8, a ratio of R/V affects the maximum percent change that can occur over a known time interval. The maximum percent change that is possible during a known time interval varies directly with the R/V ratio. However, the linearity of the line between the iniitial point ($C_i$) and the final point ($C_{(t)}$)

over a known time interval varies inversely to the R/V ratio.

If a large linear increase in concentration in the culture chamber is desired during a given time interval, the slope of a line from $C_i$ to $C_{(t)}$ is also great. Since the linearity of the increase in concentration in the culture chamber is an inverse function of the R/V ratio, large increases pose problems in reaching the point $C_{(t)}$ in a given time interval in a linear fashion. The linearity of the change in concentration can be preserved by increasing the concentration of the substance being supplied, thus not affecting the R/V ratio.

This is not the case if a large decrease in concentration in the culture chamber is desired, as the minimum concentration of a substance in a holding flask can be zero. Thus, the minimum R/V ratio (maximum linearity) must be determined. This R/V ratio is then compared with FIG. 10. To determine if the calculated R/V ratio will emulate the desired degree of linearity between the data points ($C_i$ and $C_{(t)}$) in question.

To determine the minimum R/V ratio required to achieve the percent concentration change between $C_i$ and $C_{(t)}$, the negative slope for the decreasing concentration is analyzed over a known desired time interval wherein the supply substance concentration ($C_s$) equals zero. The amount of change ($\Delta_c$) between $C_i$ and $C_{(t)}$ over the time interval t is determined by equation (7):

$$\Delta_c = \frac{C_i - C_{(t)}}{C_i} \tag{7}$$

A 100% change would occur if $C_{(t)}$ was zero ($\Delta_c = 1$). Thus, the concentration at $C_{(t)}$ would be the difference between a 100% change ($\Delta_c = 1$) and the actual change, as expressed by equation (8):

$$C_{(t)} = 1 - \Delta_c \tag{8}$$

To drive to a 100% change the supply substance concentration ($C_s$) must be zero. If the initial concentration ($C_i$) is assumed to be one, equation (8) can be substituted in equation (3), the determination of which is discussed subsequently, with $C_s = 0$ and $C_i = 1$ and an expression for the minimum R/V ratio derived:

$$C_{(t)} = C_s + (C_i - C_s)e^{-\frac{Rt}{V}} \tag{9}$$

substituting equation (2) into (3) to obtain equation (4):

$$1 - \Delta_c = 0 + (1 - 0)e^{-\frac{Rt}{V}} \tag{10}$$

simplifying:

$$1 - \Delta_c = e^{-\frac{Rt}{V}} \tag{11}$$

simplifying:

$$\ln(1 - \Delta_c) = -\frac{Rt}{V} \tag{12}$$

solving for R/V:

$$\frac{R}{V} = \frac{-1}{t} \ln(1 - \Delta_c) \tag{13}$$

substituting equation (7) into equation (13):

$$\frac{R}{V} = \frac{-1}{t} \ln\left(1 - \frac{C_i - C_{(t)}}{C_i}\right) \tag{14}$$

simplifying:

$$\frac{R}{V} = \frac{-1}{t} \ln\left(\frac{C_{(t)}}{C_i}\right) \tag{15}$$

Equation (15) provides an expression for the minimum R/V ratio required to drive to a desired concentration in a given time interval in the culture chamber. If the linearity provided by the calculated R/V ratio is not adequate to emulate a given set of data, the change in concentration can be broken into at least two steps. Assuming we wish to emulate a set of data that changes linearly from an initial concentration of $C_i$ to a final concentration of $C_{(t)}$ in a time interval of t, the first step is to break this change into two intervals. This is accomplished by setting a new point (A) at a point half way between $C_i$ and $C_{(t)}$ (i.e., at t=1/2t). Thus, secondly, a new $C_s$ in the holding flask and a new minimum R/V ratio can be calculated using $C_i$ as the initial point and changing point A to a new $C_{(t)}$ for a final point. Since the percent change required between $C_i$ and A is less than between $C_i$ and the original $C_{(t)}$, the minimum R/V will be lower and the linearity increased. This procedure can be repeated until a satisfactory linearity is achieved. In this manner, the process of the present invention emulates in-vivo conditions and other conditions and provides a method of knowing the concentration affecting the tissue at each and every point in time.

In practice, the supply substance concentration is changed using a preferred method wherein a plurality of holding flasks is used with each flask containing a different concentration ($C_s$) of the supply substance. When a different concentration of the supply drug is needed, a change is made from one holding flask to another. It will be understood by those skilled in the art that the number of flasks needed and the differences between the concentrations of the supply drug in the flasks will be a function of the particular application of the process.

Peristaltic pumps are a preferred apparatus for conveying the supply substance from the holding flasks to the culture chamber. The rate of delivery is controlled by a suitable variable speed motor and controller which drive the pump.

The known amounts removed from the culture chamber are then assayed to determine the response of the tissue to the substance. In addition, the culture chamber may be designed to accept probes, which are attached to suitable instrumentation, for monitoring pH, oxygen consumption, temperature, selective ions, membrane potentials and other variables of interest.

With the responses of the tissue known as a function of time and with the concentrations of the substance affecting the tissue also known as a function of time, relationships are established as to cause and effect, through known mathematical methods. With the immediately above-described procedure repeated and performed against "control" specimens, proper drug concentration and administration to a particular tissue are determined.

As will be appreciated by those skilled in the art, the present process is applicable to the delivery of more than one chemical stimuli at a time to the culture chamber by mixing the substances together in the same holding flask. In the case of multiple substances being utilized, the minimum R/V ratio must be determined from the greatest slope in each time interval. This result will be the same for all changes in that interval. Complex experiments, heretofore not possible, may be carried out in-vitro emulating known in-vivo and other conditions by use of the present invention. In-vitro conditions are adjustable at will and the responses observable without costly live animal experimentation. In addition, unwanted interference from bodily responses to experimentation directed at the particular tissue is eliminated thereby reducing the number of experiments needed to achieve statistical reliability.

Once the relationships between chemical stimuli and tissue are determined, the process is used to deliver the chemical stimuli to subsequent tissue in an optimal manner. For example, organ transplants are kept biologically alive longer using the process to deliver nutrients at a rate and concentration as the transplant needs the nutrients.

Another important advantage of the process of the present invention is that it is particularly well suited for control by electronic means such as a programmed digital computer together with appropriate interface circuitry. More specifically, the administration of the rate of delivery and the concentrations of the chemical stimuli supplied to the tissue are controllable by a suitable microprocessor-based control system. Once programmed with the desired changes in concentration with respect to time, the microprocessor manipulates the process apparatus, such as the peristaltic pump. If a plurality of flasks are used to hold different concentrations of the chemical stimuli, then the switching from flask to flask is controlled through the microprocessor.

Although the present invention has been described with reference to preferred embodiments, workers skilled in the art will recognize that changes may be made in form and detail without departing from the spirit and scope of the invention.

What is claimed is:

1. An apparatus for delivering a controlled dosage of a chemical substance to a cell culture, the apparatus comprising:
   a plurality of vessels, each vessel containing a different known concentration of the same chemical substance;
   valving means having a plurality of inlet and a single outlet and having means for selectively connecting in fluid communication a preselected inlet to the single outlet;
   first conduit means for fluidly connecting each vessel to a corresponding inlet of the valving means;
   cell culture means for containing a cell culture, said cell culture means being in fluid connection with the outlet of the valving means and having an initial concentration of the chemical substance;
   second conduit means for fluidly connecting the single outlet of the valving means to the cell culture means;
   means for providing a transport force to the chemical substance in a flow controlled manner for delivering the chemical substance to the cell culture means and being in fluid communication with the outlet of the valving means and the cell culture means; and
   control means for controlling the valving means having means for providing input signals and means for providing signals indicative of a desired program of administration such that a preselected inlet is fluidly connected to the outlet for presenting a first preselected known concentration of the chemical substance to the cell culture means, and for controlling the means for providing a transport force to the chemical substance to effect a selected rate of delivery, including means for controlling the concentration of the chemical substance in the cell culture means according to the program of administration corresponding to the equation $$C_{(t)} = C_s + (C_i - C_s)e^{-\frac{Rt}{V}}$$

wherein
   t = integration time interval
   V = volume of fluid within the cell culture means in which the chemical substance is being delivered
   R = the rate of delivery of the chemical substance to the cell culture means
   $C_i$ = the initial concentration level of the chemical substance in the integration time interval within the cell culture means
   $C_{(t)}$ = the final concentration of the chemical substance in the integration time interval within the cell culture means
   $C_s$ = the concentration of the chemical substance being delivered in the integration time interval from the vessels into the cell culture means
wherein the means for controlling the concentration selects values of R/V and $C_s$ such that the concentration change between $C_i$ and $C_{(t)}$ is linear and the control means for controlling the valving means selectively switches among the vessels to choose $C_s$ for each integration time interval in response to the desired program of administration.

2. The apparatus of claim 1 wherein the cell culture means is a culture chamber having an inlet fluidly connected to the second conduit means and an outlet.

3. The apparatus of claim 2 and further including means for collecting the chemical substance connected to the outlet of the culture chamber.

4. The apparatus of claim 3 and further including analyzer means for analyzing the chemical substance after being collected by the means for collecting.

5. The apparatus of claim 3 and further including means for sterily collecting the chemical substance in the means for collecting.

6. The apparatus of claim 2 and further including gas delivery means for delivering gas to the chemical substance in the plurality of vessels.

7. The apparatus of claim 6 wherein the gas delivery means includes diffusion means for diffusing the gas within each vessel.

8. The apparatus of claim 1 wherein the control means includes a programmed digital computer system.

9. The apparatus of claim 1 wherein the valving means includes means for maintaining a sterile seal to all inlets not connected to the outlet.

10. The apparatus of claim 1 wherein the valving means has twelve inlets.

11. The apparatus of claim 1 wherein the means for providing a transport force is a pump.

12. The apparatus of claim 11 wherein the pump is a peristaltic pump.

13. The apparatus of claim 12 wherein the peristaltic pump has a flow delivery rate accuracy of ±0.01 milliliters in any time interval.

14. An apparatus comprising:
a plurality of different source concentrations of a chemical substance;
valving means having a plurality of inlets and a single outlet for fluidly connectng a preselected inlet to the single outlet and having means for selectively connecting in fluid communication a selected single inlet with the outlet;
first conduit means for fluidly connecting each source concentration to a corresponding inlet of the valving means;
a chamber for receiving the chemical substance in a controlled manner and environment being in fluid communication with the outlet of the valving means and having an initial concentration of the chemical substance;
second conduit means for fluidly connecting the single outlet of the valving means to the chamber;
means for providing a transport force to the chemical substance in a flow controlled manner for delivering the chemical substance to the chamber being in fluid communication with the outlet of the valving means; and
control means for controlling the valving means having means for providing input signals and means for providing signals indicative of a desired program of administration such that a preselected inlet is fluidly connected to the outlet for presenting a first preselected known concentration of the chemical substance to the chamber, and for controlling the means for providing a transport force to the chemical substance to effect a selected rate of delivery, including means for controlling the concentration of the chemical substance in the chamber according to the program of administration corresponding to the equation $$C_{(t)} = C_s + (C_i - C_s)e^{-\frac{Rt}{V}}$$

wherein
t = the integration time interval
V = volume of fluid within the chamber in which the chemical substance is being delivered
R = the rate of delivery of the chemical substance to the chamber
$C_i$ = the initial concentration level of the chemical substance in the integration time interval within the chamber
$C_{(t)}$ = the final concentration of the chemical substance in the integration time interval within the chamber
$C_s$ = the concentration of the chemical substance being delivered in the integration time interval from the source concentration into the chamber
wherein the means for controlling the concentration selects values of R/V and $C_s$ such that the concentration change between $C_i$ and $C_{(t)}$ is linear and the control means for controlling the valving means selectively switches among the source concentrations to choose $C_s$ for each integration time interval in response to the desired program of administration.

15. The apparatus of claim 14 wherein the control means includes a computer control system.

16. The apparatus of claim 15 wherein the computer control system controls the environment in the chamber.

17. The apparatus of claim 14 and further comprising at least one sensing input for providing signals to the control means.

18. The apparatus of claim 17 wherein the sensing input is a pH sensor for sensing pH within the chamber.

19. The apparatus of claim 19 wherein the sensing input is an oxygen sensor for sensing oxygen content within the chamber.

20. The apparatus of claim 14 and further comprising operator input means for inputting concentration parameters to the control means.

* * * * *

UNITED STATES PATENT AND TRADEMARK OFFICE
CERTIFICATE OF CORRECTION

PATENT NO. : 4,629,686

DATED : December 16, 1986

INVENTOR(S) : Micheal L. Gruenberg

It is certified that error appears in the above-identified patent and that said Letters Patent is hereby corrected as shown below:

In claim 1, col. 13, line 56, the word "inlet" should read --inlets--.

In claim 14, col. 15, line 17, the word "connectng" should read --connecting--.

In claim 19, col. 16, line 40, "19" should read --17--.

Signed and Sealed this

Third Day of March, 1987

Attest:

DONALD J. QUIGG

Attesting Officer

Commissioner of Patents and Trademarks